(12) United States Patent
Boronkay et al.

(10) Patent No.: US 7,727,477 B2
(45) Date of Patent: Jun. 1, 2010

(54) APPARATUS FOR PRIMING MICROFLUIDICS DEVICES WITH FEEDBACK CONTROL

(75) Inventors: Allen Boronkay, San Jose, CA (US); Colin Kennedy, Greenbrae, CA (US); Matthew Latham, Dixon, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 593 days.

(21) Appl. No.: 11/288,838

(22) Filed: Nov. 28, 2005

(65) Prior Publication Data

US 2006/0163070 A1 Jul. 27, 2006

Related U.S. Application Data

(60) Provisional application No. 60/635,223, filed on Dec. 10, 2004.

(51) Int. Cl.
*G01N 1/00* (2006.01)
*G01N 21/01* (2006.01)

(52) U.S. Cl. .................. 422/100; 422/60; 422/103; 422/104; 422/63; 436/43; 436/174; 436/180

(58) Field of Classification Search ............ 422/63–65, 422/99–100; 436/49, 50, 54, 55, 180; 73/863.01–863.03, 73/863.11, 864.01, 864.41, 864.13
See application file for complete search history.

(56) References Cited

U.S. PATENT DOCUMENTS

| | | | | |
|---|---|---|---|---|
| 5,112,575 A * | 5/1992 | Whitehouse et al. | ......... | 422/116 |
| 5,519,635 A * | 5/1996 | Miyake et al. | ............. | 700/285 |
| 5,571,410 A * | 11/1996 | Swedberg et al. | ........ | 210/198.2 |
| 5,585,069 A * | 12/1996 | Zanzucchi et al. | .......... | 422/100 |
| 5,603,351 A * | 2/1997 | Cherukuri et al. | ........... | 137/597 |
| 5,800,690 A * | 9/1998 | Chow et al. | .................. | 204/451 |
| 5,876,675 A * | 3/1999 | Kennedy | ...................... | 422/99 |
| 5,955,028 A * | 9/1999 | Chow | ........................... | 422/63 |
| 5,965,410 A * | 10/1999 | Chow et al. | ................. | 435/91.2 |
| 5,989,402 A * | 11/1999 | Chow et al. | ................. | 204/601 |
| 6,409,832 B2 * | 6/2002 | Weigl et al. | ................. | 117/206 |
| 6,495,104 B1 * | 12/2002 | Unno et al. | ................ | 422/68.1 |
| 6,756,019 B1 * | 6/2004 | Dubrow et al. | .............. | 422/102 |
| 6,811,668 B1 * | 11/2004 | Berndt et al. | ................ | 204/601 |
| 6,976,364 B1 * | 12/2005 | Bengtsson | ..................... | 62/3.7 |
| 7,160,423 B2 * | 1/2007 | Chien et al. | ................. | 204/453 |
| 2001/0041357 A1 * | 11/2001 | Fouillet et al. | ............. | 435/91.1 |
| 2001/0052460 A1 * | 12/2001 | Chien et al. | ................. | 204/450 |

(Continued)

FOREIGN PATENT DOCUMENTS

FR 2799139 A1 4/2001

(Continued)

*Primary Examiner*—P. Kathryn Wright
(74) *Attorney, Agent, or Firm*—Townsend and Townsend and Crew LLP.; M. Henry Heines

(57) ABSTRACT

A priming unit for a microfluidics device contains a pressurization unit and pressure and temperature detectors as part of a feedback loop that controls the pressure applied by the pressurization unit and the time during which the pressure is applied. This control feature is particularly useful in controlling the exposure time of the microchannels to dyes in the priming liquids since certain dyes tend to adhere to the walls of the channels and produce non-uniform results.

11 Claims, 5 Drawing Sheets

U.S. PATENT DOCUMENTS

2002/0176804 A1* 11/2002 Strand et al. ............... 422/100
2005/0019213 A1* 1/2005 Kechagia et al. ............. 422/57
2005/0024644 A1* 2/2005 Mototsu et al. ............. 356/436
2005/0232817 A1* 10/2005 Ahn et al. ..................... 422/99
2006/0198766 A1* 9/2006 Muller et al. ............... 422/104
2006/0275179 A1* 12/2006 Viovy et al. ................ 422/100

FOREIGN PATENT DOCUMENTS

FR 2855076 A1 11/2004

* cited by examiner

APPARATUS FOR PRIMING MICROFLUIDICS DEVICES WITH FEEDBACK CONTROL

CROSS REFERENCE TO RELATED APPLICATION

This application claims benefit from U.S. Provisional Patent Application No. 60/635,223, filed Dec. 10, 2004, the contents of which are incorporated herein by reference in their entirety.

BACKGROUND OF THE INVENTION

1. Field of the Invention

This invention resides in the field of microfluidics, and in particular to certain features of an automated priming unit designed to fill the channels of a microfluidics device with liquids or gels. The invention is of particular interest to "lab-on-a-chip" systems for automated electrophoresis.

2. Description of the Prior Art

Electrophoresis is one example of a laboratory procedure that can be performed in an automated manner in a microfluidics device. Other examples are micro-scale binding assays and simulations of various processes and phenomena such as fluid dynamics, structural dynamics, thermal dynamics, and reaction kinetics. As a representative example, electrophoresis typifies the uses and advantages of microfluidics. The typical microfluidics device for electrophoresis is a small glass plate (or "chip") affixed to a plastic carrier. The glass plate contains an array of microchannels in a network pattern that has been designed for optimum effect in electrophoresis. The various procedures involved in an electrophoretic analysis are performed by directing materials through the microchannels for purposes such as sample injection, separation, staining, and destaining. All of these procedures, plus detection and data analysis, are performed without user intervention. The components of the system as a whole, in addition to the chip and carrier, typically include an electrophoresis station which houses the electrical, optical, and hardware components needed to perform the electrophoresis, a priming station on which chips are loaded with appropriate liquids or gels and prepared for electrophoresis, a vortex station where samples and loading buffers are mixed inside the wells of the chip, software for system operation and data processing, and analysis kits for specific types of separations.

The typical microfluidics device for electrophoresis is a chip or block that contains an interconnected network of microchannels. One such device is shown in an exploded perspective view in FIG. 1 and in a side view in FIG. 2. The device 11 has a planar, layered body structure consisting of at least two layers, an upper layer 12 and a lower layer 13, bonded together. The upper surface 14 of the lower layer 13 is etched or otherwise cut or molded to contain a pattern of grooves 15. When the two layers are joined, these grooves form the microchannels within the chip that will contain the gel or other separation medium in which electrophoresis is to be performed. Apertures 16 in the upper layer provide expanded openings for access to the microchannels when the two layers are combined. FIG. 1 shows sixteen apertures in a 4×4 array. When such a device is used for electrophoresis, the separation medium, frequently in the form of a viscous liquid, is placed in one of the sixteen apertures, typically an aperture in one of the four corners of the array. The other apertures are often reserved for other liquids used in the electrophoretic procedure, such as buffers, staining solutions, and samples.

In use, the microfluidics device 11 of FIGS. 1 and 2 is enclosed in a carrier 21, commonly termed a "caddy." A typical such carrier is shown in FIG. 3. The carrier fully encases the microfluidics device and thereby removes the device from visibility in this view. The shape of the carrier can vary and will be selected to coordinate its use with the remaining units and components with which the microfluidics device is used. The caddy shown in FIG. 3 is generally rectangular with two curved opposing edges 22, 23. The carrier contains an array of cylindrical extensions 24 with the same spacing and arrangement as the apertures 16 (FIG. 1) of the microfluidics device and these extensions are aligned with the apertures when the microfluidics device is inserted in the carrier. These extensions serve as reservoirs over the apertures to hold the gel or liquid that will pass through the apertures into the microchannels when pressure is applied. Although not shown, the carrier 21 also contains various structural and connecting features that permit electrophoresis (or other procedures) to be performed on the fluids that will be placed in the microchannels without removing the microfluidics device from the carrier.

One factor that affects the reliability, reproducibility, and ease of use of a microfluidics device is the manner in which the microchannels are primed with the gel or any of the liquids needed for the electrophoretic analysis. It is known, for example, that dyes in separation matrices tend to bind to the walls of the microchannels during priming. Wall-bound dye in the detection channel becomes background signal that adversely affects the detection sensitivity of the instrument and causes nonuniformity between different chips. Chips intended for use with matrices containing RNA, for example, are particularly susceptible to dye binding due to the cationic nature of the RNA dye. In general, differences in the amounts of dye bound to the walls can be minimized or eliminated by controlling the time during which the walls are exposed to dye. In chips used for protein analyses, for example, a common practice is to limit the priming time to a maximum of one minute. In chips used for analyses of other species, such as nucleic acids, a shorter maximum priming time may be required. The present invention offers several features that facilitate the priming process and provide improved control over the exposure time as well as the amounts of gel or liquid that are placed in the microchannels.

SUMMARY OF THE INVENTION

The present invention resides in a priming unit for a microfluidics device, the priming unit containing a pressurization unit, a pressure detector, and preferably a temperature detector as well, plus a feedback loop to receive signals from the detector(s) and process the signals to provide a pressure vs. time profile that will result in full priming of the microfluidics device based on the viscosity characteristics of the priming fluid, without excess exposure time. In preferred embodiments of the invention, specialized features of construction contribute further to the economy and efficiency of the priming unit. One example of such a feature is a barrel and motorized plunger to apply air pressure to the reservoirs that contain the priming fluid and feed the microchannels. Another is the combination of the barrel, a mount for the plunger motor, and a mount for the pressure detector in a single piece, such as an injection molded part. Still another is an innovative seal at the site where the piston barrel contacts a reservoir in the carrier, that can be readily removed and replaced when worn. These and other features, objects and advantages of the invention and its use will be apparent from the description that follows.

DETAILED DESCRIPTION OF THE INVENTION AND PREFERRED EMBODIMENTS

While the invention is susceptible to a wide range of configurations and embodiments, the underlying concepts and principles of the invention and its novel aspects can be understood by a detailed review of a specific embodiment. One such embodiment is depicted in FIGS. 4, 5, and 6 and described below.

Figure 1:
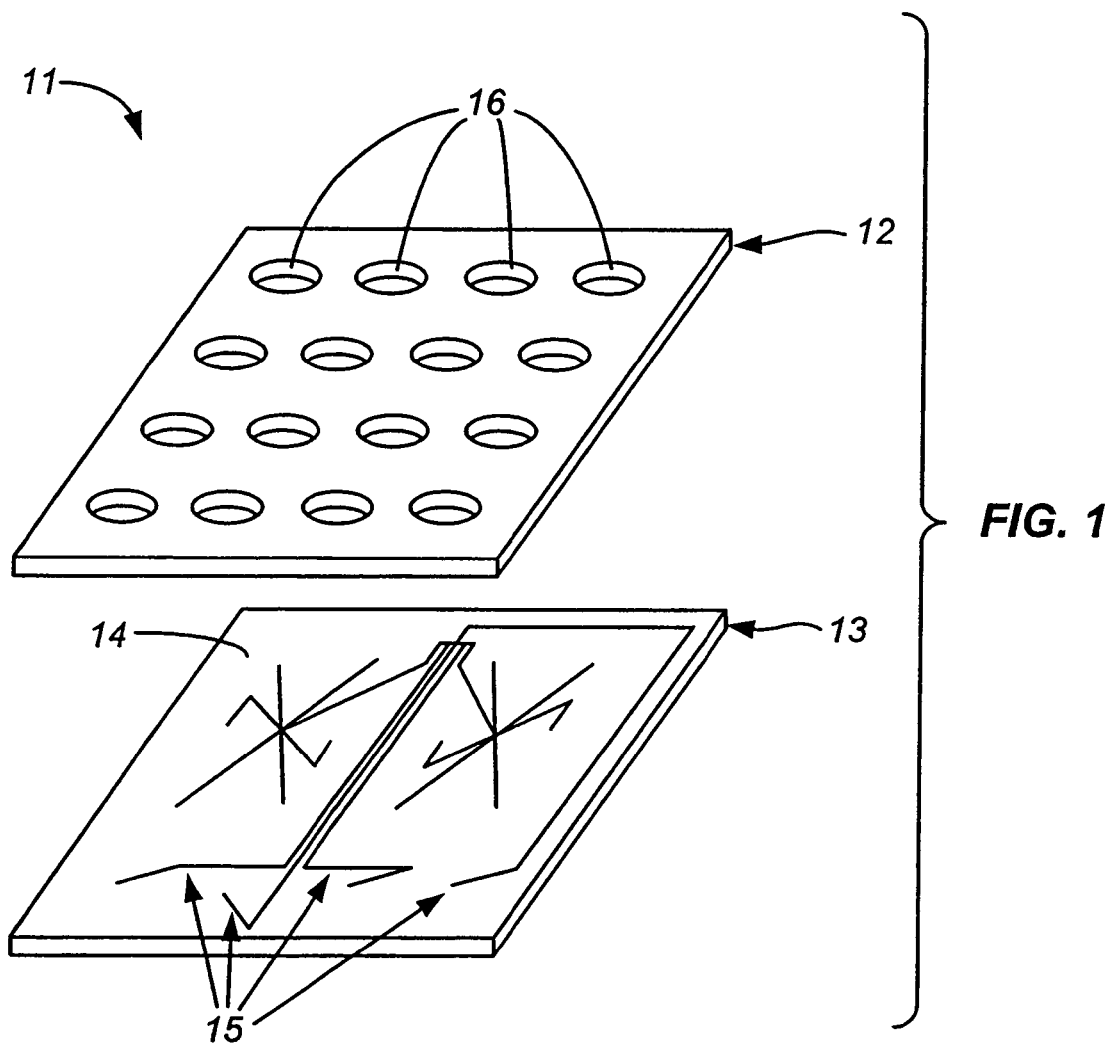
FIG. 1 (representing prior art) is an exploded view of a microfluidics device to which the present invention can be applied.
Figure 2:
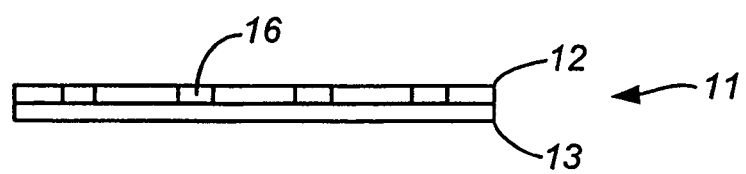
FIG. 2 (representing prior art) is an end view of the microfluidics device of FIG. 1 as assembled.
Figure 3:
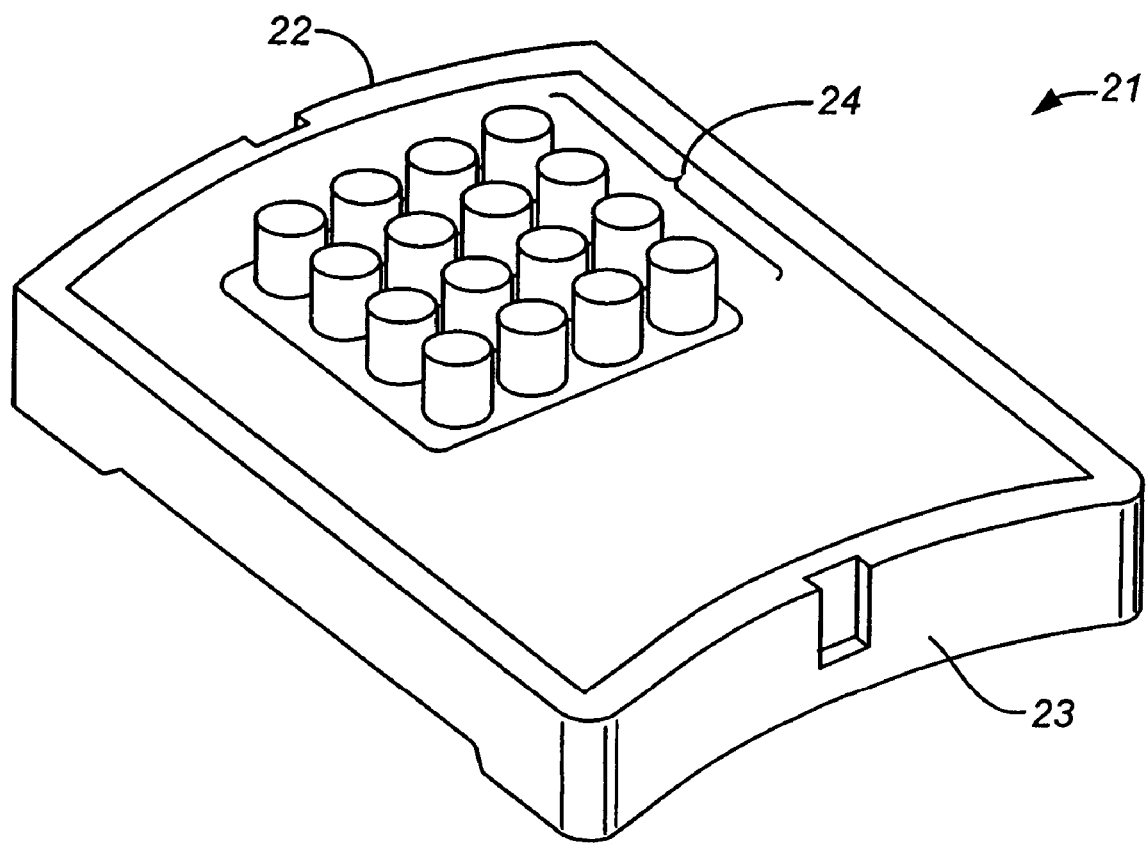
FIG. 3 (representing prior art) is a perspective view of a carrier for the microfluidics device of FIG. 1.
Figure 4:
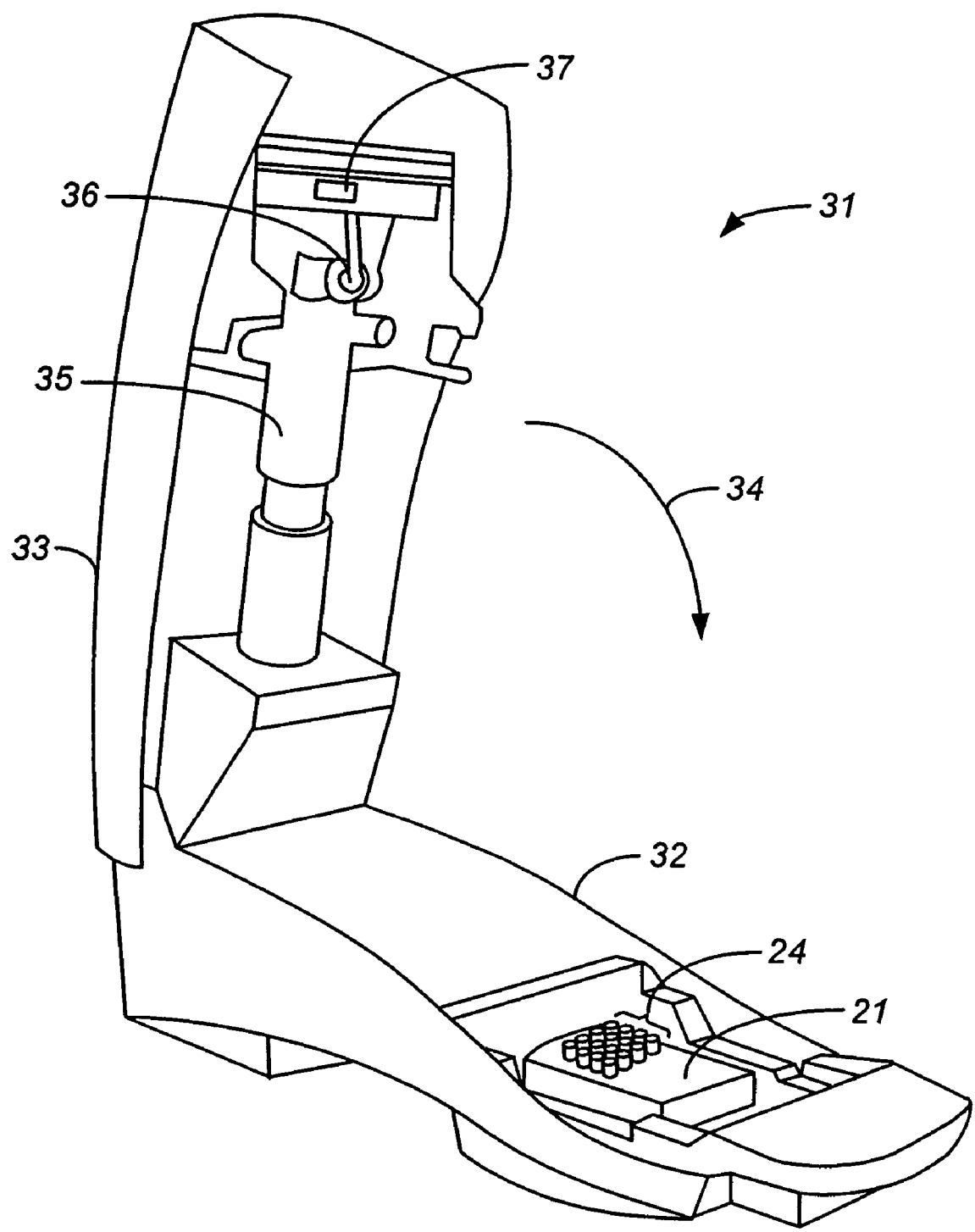
FIG. 4 is a perspective view of a priming unit in accordance with the present invention.

The priming unit 31 of FIG. 4 includes a base 32 and a top 33, joined by a hinge connection at the rear of the base. The unit is shown in an open position, and is closed by rotating the top down in the direction of the arrow 34. To prepare the unit for priming of a microfluidics device, one or more of the reservoirs of the carrier holding the microfluidics device is filled with the priming fluid, whether the fluid be a gel or liquid. This can be done by pipette either before or after the carrier has been placed inside the priming unit but before the priming unit has been closed over the carrier. Once the priming unit is closed, the supply lines in the priming unit are engaged with the microfluidics device in the carrier. The priming unit forms a pressure seal over the reservoirs, thereby sealing the fluid in the reservoirs and allowing the reservoirs to be pressurized with pressure generated inside the priming unit. The pressure forces the liquid in the reservoirs into the microchannels of the microfluidics device. The pressure is supplied as air pressure generated by a plunger moving within a barrel inside the priming unit and driven by a motor. Electric motors, and particularly stepper motors, are examples of suitable motors. The force generated by the motor is transmitted to the plunger by any conventional means; one example is a lead screw.

The carrier 21 holding the microfluidics device is shown in position in the base 32 where the microfluidics device is secured in position by appropriate fastening fixtures or mating contours, or both. The cylindrical extensions 24 on the carrier, which as noted above serve as reservoirs for the priming liquid or gel, are exposed and open upward. Mounted in the top 33 of the priming unit is a motor-driven pressurization component 35 with an interfacing seal 36 that serves as a delivery port through which pressure is transmitted from the pressurization component to the appropriate cylindrical extension 24 in the carrier 21 and thus to the aperture underneath. The application of pressure forces liquid in the cylindrical extension to enter the channels in the microfluidics device.

Figure 5:
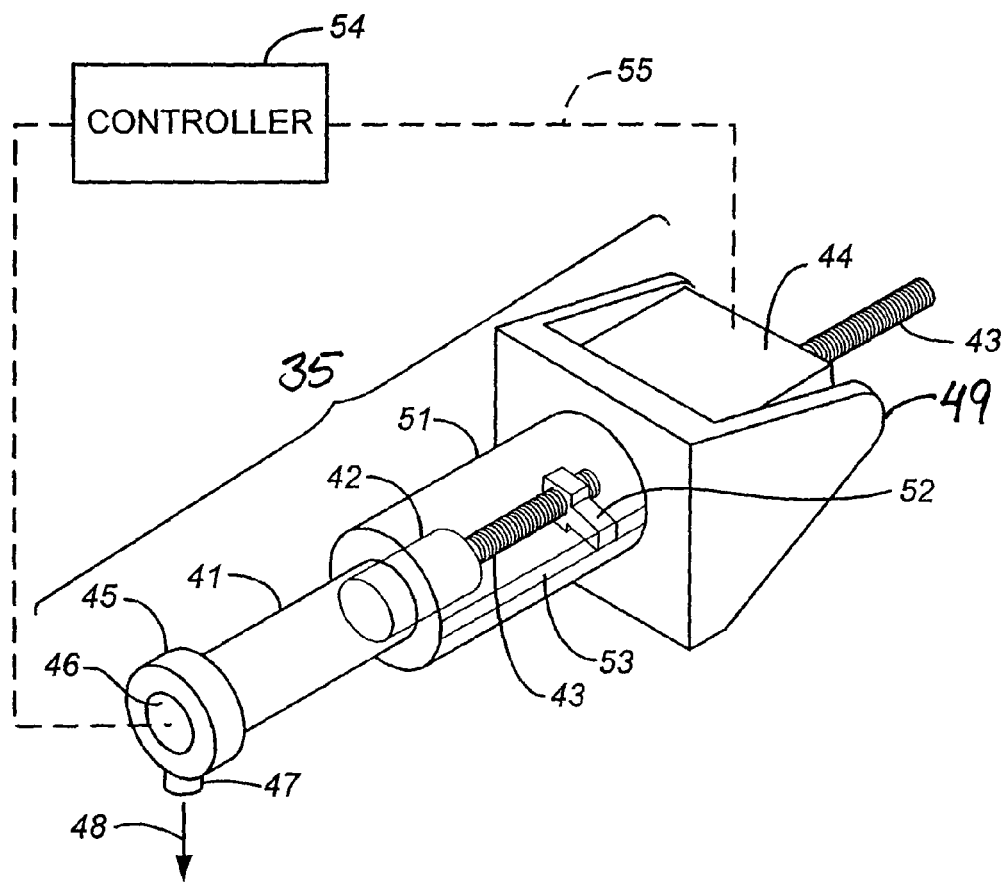
FIG. 5 is a perspective view of a pressurization unit within the priming unit of FIG. 4.
Figure 6:
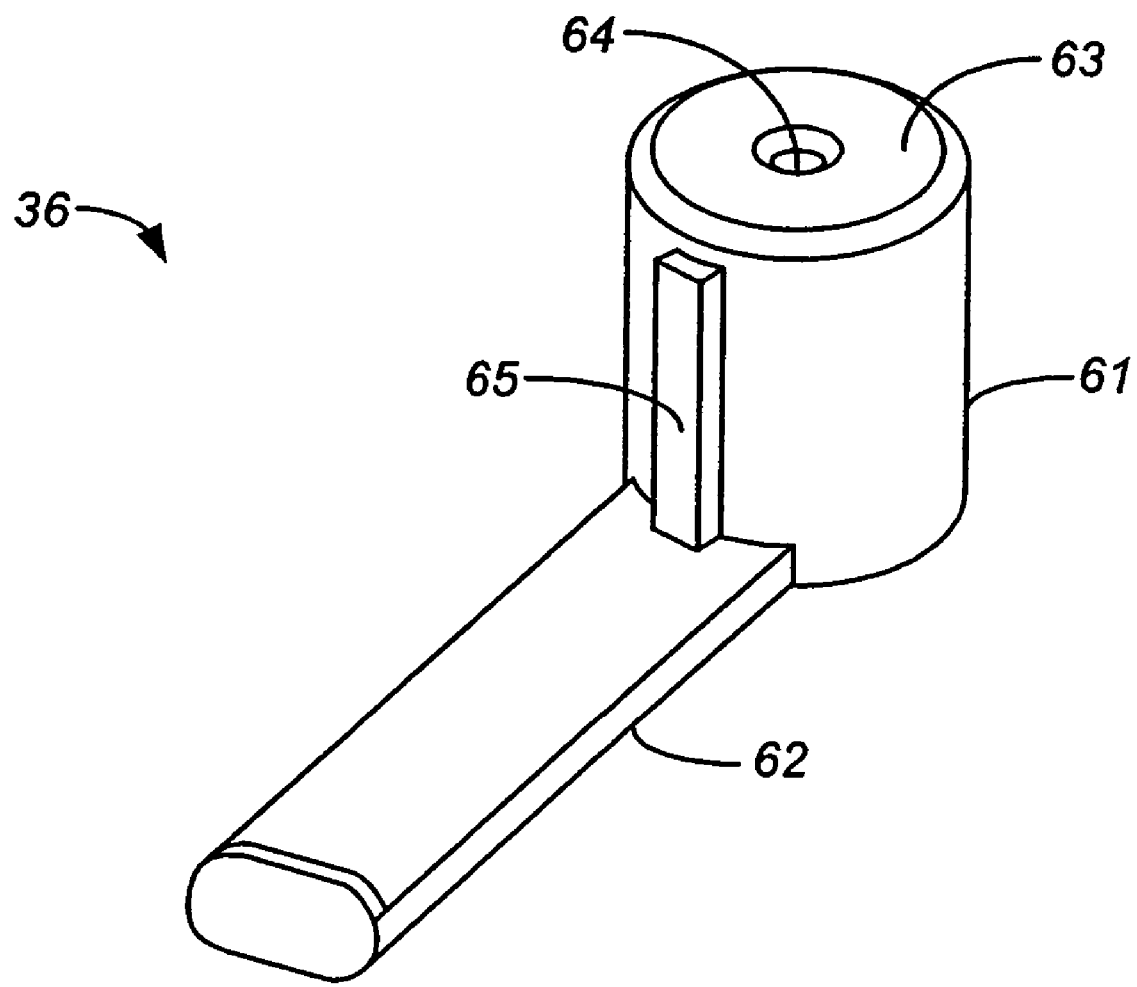
FIG. 6 is a perspective view of an interface seal within the priming unit of FIG. 4.

FIG. 5 is an enlarged view of the pressurization component 35. The component is preferably a unitary molded plastic part formed by injection molding or other conventional casting, machining, or molding techniques. The component shown in this FIG. is transparent and consists of a barrel 41, a plunger 42 that moves axially inside the barrel, a lead screw 43 to control the position of the plunger 42, and a motor 44 to drive the lead screw. As noted above, the motor 44 can be any conventional motor capable of highly controlled movements in small increments. Linear stepper motors are examples of suitable motors. The exit end 45 of the barrel is enlarged to form a mount for a pressure transducer 46, with the sensing surface of the transducer facing inside the barrel. A boss 47 on one side of the barrel exit end 45 serves as a pressure application outlet, providing a conduit for transmission of the internal barrel pressure outward, in the direction indicated by the arrow 48, to the receiving cylindrical extension on the microfluidics device carrier, and thereby serves as an interface for contact with the reservoir described above. The barrel 41, a mount 49 for the motor, and the mount 45 for the pressure transducer are integrated into a single injection-molded part.

At the entry end of the barrel 41 is an enlarged housing 51 for the travel of the lead screw 43. Affixed to and projecting laterally from the lead screw is a follower 52, such as a tab or pin, which extends into a groove or slot 53 in the wall of the housing 51. As the lead screw 43 moves axially in response to the motor 44, the follower 52 travels inside the groove or slot 53. The follower 52 prevents the lead screw 43 from rotating as the lead screw is driven by the motor, thereby restricting the lead screw movement to a linear travel. Further securement of the lead screw orientation can be achieved by the use of a two-sided follower. The follower 52 can also be configured to trip switches at one or both ends of the travel range of the lead screw to limit the travel of the plunger 42.

FIG. 6 is an enlarged view of the interfacing seal 36. The seal consists of a cylindrical plug portion 61 and a tab 62. The tab is used for manual handling of the seal for purposes of insertion, removal, and replacement. The plug portion 61 fits inside the boss 47 of the pressurization component (FIG. 5). The upper surface 63 of the plug portion is rounded or toroidal in shape and resilient to form an o-ring type seal against the boss interior. A central passage 64 through the plug allows the transmission of pressure through the plug to the underlying carrier and microfluidics device. An external rib 65 mates with a groove or notch in the boss interior to control the orientation of the seal.

Returning to FIG. 5, a controller 54 forms part of a single feedback loop 55 that joins the pressure transducer 46 and the motor 44 and that provides automatic control of the pressure applied to the reservoirs. A target pressure or a pressure-time profile or integral can be pre-selected and applied to a reservoir by means of a control algorithm, an example of which is a dead-band algorithm. Preferably, the algorithm applies a pre-selected integral of pressure vs. time to a reservoir to place a specified volume of liquid in the reservoir, and the motor is driven in accordance with the algorithm. The integral can be a simple product of pressure×time for a constant pressure or an integral of varying pressure over time. Once the priming is done, the plunger is returned to its starting position and the unit is opened to disengage the barrel from the microfluidics carrier. Controls based on an integral of pressure vs. time rather than pressure alone allow the system to make adjustments in the pressure application time to compensate for errors or variations in the applied pressure.

An alternative to the barrel and plunger is a bladder, a fluid source supplying fluid such as air, an aqueous liquid, or an oil to the bladder, and a controllable, variable-speed pump between the fluid source and the bladder. The pumping of fluid to the bladder will cause expansion of the bladder which is then transmitted to the cylindrical extensions 24 as a controlled increased in pressure. Other alternatives will be apparent to those skilled in the art.

Returning to FIG. 4, a temperature sensor 37 is mounted to the interior of the priming unit 31. The temperature sensor 37 is placed sufficiently close to the site where the carrier 21 is to be mounted that the temperature sensed is the same as that of the carrier and the liquids in the carrier reservoirs. The temperature thus detected is indicative of the viscosity by known relations for any given liquid or gel, and serves as a means for compensating for temperature-induced variations of viscosity. A precision integrated-circuit temperature sensor, examples of which are known in the art, will provide the degree of precision needed for viscosity control. The temperature detected by the sensor is processed by a firmware calculation by the same controller 54 depicted in FIG. 5, and preferably in the same control loop. The controller 54 incorporates the temperature signal into the algorithm and adjusts the motion or position of the plunger 42 accordingly. Temperature variations can be compensated for by adjustments in the pressure level, the pressure application time, or both. The temperature can be measured either in the priming unit or in the surrounding atmosphere, and transmitted to a control unit that operates the motor driving the piston in the priming unit. Using an internal temperature of 22° C. as a nominal set point, for example, each increase in temperature of one degree Celsius for certain gels will be compensated for by a 3% lowering of pressure (expressed as percent of gauge pressure). Other temperature-pressure (i.e., viscosity-temperature) relationships will hold for other gels, some linear and others nonlinear. The relationship for any particular liquid or gel is readily determinable by routine experimentation. Different nominal pressure settings can be used for different microfluidics devices. Thus, three different devices can have nominal pressure settings of 50 psi, 75 psi, and 100 psi, respectively (all gauge). For certain gels, as noted above, the automated adjustment will therefore vary the pressure from each of these starting points by 3% for every one-degree variation from 22° C.

Certain embodiments of the invention contain additional features. One such feature is a vent hole in the barrel at a location near the beginning of the piston stroke. This vent hole allows the pressure on the plunger to return to ambient or atmospheric pressure after every stroke. Another feature is to use a barrel shaped to minimize the volume of the barrel that is not swept by the plunger and thereby to minimize the amount of dead volume within the system. This maximizes the pressure that can be reached for a given barrel volume. Another feature that will provide a benefit in certain embodiments is the use of seals that are removable without the use of tools. Thus removed, the seals are readily cleaned or replaced. In certain embodiments as well, the lead screw nut is integral with the motor.

The foregoing is offered primarily for purposes of illustration. Variations in the configurations, shapes and physical arrangements of the priming unit and its components can be made while still utilizing the concepts and features that distinguish this invention from the prior art. These variations will be apparent to those skilled in the art and are intended to be included within the scope of this invention.

What is claimed is:

1. Apparatus for priming a microchannel network in a microfluidics block with liquid, said apparatus comprising:
   a carrier having at least one reservoir and configured to receive said microfluidics block with said reservoir in fluid communication with said microchannel network;
   a priming unit configured to enclose said carrier with said microfluidics block received within said carrier and to force liquid from said reservoir into said microchannel network, said priming unit comprising pressure applying means for applying pressure to said reservoir, means for detecting pressure so applied, and a feedback loop providing automated control of said pressure applying means based on pressure so detected to cause said priming unit to pressurize said reservoir at a pressure level and a pressurization time that will cause a selected amount of liquid to pass from said reservoir into said microchannel network.

2. The apparatus of claim 1 wherein said means for applying pressure to said reservoir comprise a barrel and a motor-driven plunger.

3. The apparatus of claim 2 wherein said motor-driven plunger is driven by a stepper motor.

4. The apparatus of claim 2 wherein said motor-driven plunger comprises a plunger and a motor operatively joined to said plunger by a lead screw.

5. The apparatus of claim 1 wherein said means for detecting pressure is a pressure transducer.

6. The apparatus of claim 2 wherein said barrel, a mount for said motor, and a mount for said pressure detecting means are integrated into a single, injection-molded part.

7. The apparatus of claim 2 wherein said barrel has an outlet end through which pressure is transmitted to said reservoir, and said means for detecting pressure is a pressure transducer is positioned at said outlet end.

8. The apparatus of claim 1 further comprising means for detecting the temperature of said carrier, and wherein said feedback loop receives signals representative of both said temperature so detected and said pressure so detected and governs said pressure applying means based on both said signals.

9. The apparatus of claim 2 wherein said barrel has an outlet end with an interface for contact with said reservoir, said apparatus further comprising a manually removable pressure seal at said interface.

10. The apparatus of claim 9 wherein said interface is a boss to receive said manually removable pressure seal, and said barrel, a mount for said motor, a mount for said pressure detecting means, and said boss are integrated into a single, injection-molded part.

11. The apparatus of claim 1 wherein said feedback loop comprises a controller programmed to control pressure level and duration in accordance with an integral of pressure vs. time selected to cause passage of said selected amount of liquid.

* * * * *